(12) United States Patent
Woias et al.

(10) Patent No.: US 6,490,034 B1
(45) Date of Patent: Dec. 3, 2002

(54) MICROMECHANICAL TRANSMISSION MEASURING CELL

(75) Inventors: Peter Woias, München (DE); Bernd Hillerich, Ulm (DE)

(73) Assignee: Fraunhofer-Gesellschaft zur Foerderung der angewandten Forschung e.V., Munich (DE)

( * ) Notice: Subject to any disclaimer, the term of this patent is extended or adjusted under 35 U.S.C. 154(b) by 0 days.

(21) Appl. No.: 09/308,170

(22) PCT Filed: Nov. 11, 1997

(86) PCT No.: PCT/EP97/06278

§ 371 (c)(1),
(2), (4) Date: Jun. 11, 1999

(87) PCT Pub. No.: WO98/22803

PCT Pub. Date: May 28, 1998

(30) Foreign Application Priority Data

Nov. 18, 1996 (DE) .......................... 196 47 644
Dec. 27, 1996 (DE) ...................... 296 22 495 U (51) Int. Cl.[7] ............................ G01N 1/10; G01N 21/01
(52) U.S. Cl. ...................................... 356/246; 356/440
(58) Field of Search ............................... 356/246, 244, 356/440; 422/82.05, 82.09; 436/165; 250/428

(56) References Cited

U.S. PATENT DOCUMENTS

| 4,908,112 A | 3/1990 | Pace |
| 5,439,647 A | 8/1995 | Saini |
| 5,489,988 A | 2/1996 | Ackley et al. |

FOREIGN PATENT DOCUMENTS

| CH | 674 082 A5 | 4/1990 |
| DE | 39 42 325 A1 | 6/1991 |
| DE | 41 37 060 A1 | 5/1993 |
| EP | 0 488 947 A1 | 6/1992 |
| GB | 2 071 355 A | 9/1981 |
| JP | 2-32232 A | 2/1990 |
| WO | WO 93/22053 | 11/1993 |
| WO | WO 95/23331 | 8/1995 |
| WO | WO-96-34282 | 10/1996 |

OTHER PUBLICATIONS

Sobek et al., "A Microfabricated Flow Chamber For Optical Measurements In Fluids," IEEE Micro Electro Mechanical Systems, IEEE Robotics & Automation Society (Ft. Lauderdale, FL), pp. 219–224 (Feb. 7–10, 1993).

Verpoorte et al., "A Novel Optical Detector Cell for Use in Miniaturized Total Chemical Analysis Systems," IEEE, pp. 796–799 (1991).

Yacoub–George et al., "A Miniaturized ISFET–ELISA System With a Pretreated Fused Silica Capillary As Reaction Cartridge," The 8th Int. Conf. on Solid–State Sensors and Actuators, and Eurosensors IX (Stockholm, Sweden), pp. 898–901 (Jun. 25–29, 1995).

*Primary Examiner*—F. L. Evans
*Assistant Examiner*—Zandra Smith (57) ABSTRACT

A micromechanical transmission measuring cell serves to determine an optical absorption of a sample fluid or as a reactor for carrying out an optically detectable chemical reaction. The micromechanical transmission measuring cell comprises a receptacle (12) used for holding the sample fluid, a light passage opening (30) for introducing the light into the receptacle (12), and a reflector (26) directing the light relative to the receptacle (12) in such a way that most of said light (24) passes through said receptacle (12) without multiple reflections on a wall of said receptacle (12), and that the optical absorption of the sample fluid is detectable on the basis of the light passing through said receptacle without multiple reflections.

15 Claims, 6 Drawing Sheets

MICROMECHANICAL TRANSMISSION MEASURING CELL

The present invention relates to optical transmission measuring cells and reactors with an integrated optical detection mechanism and, especially, to a micromechanical transmission measuring cell for determining an optical absorption of a sample fluid.

Reactors with an without integrated evaluation components are presently used in various fields of analytical and synthetic chemistry. One embodiment which is frequently used in the field of analytical chemistry is the microtitration plate, which is used for immunological testing methods, e.g. the enzyme-linked immunosorbent assay (ELISA). Microtitration plates normally consist of an optically transparent plastic body provided with a number of depressions used as reaction vessels. The inner wall of said reaction vessels is coated with a suitable biochemical receptor layer which, when the sample fluid has been filled in, permits selective bonding of the analyte molecule to be determined to at least one reactor wall. In further reaction steps, a change in colour is produced in the reaction vessel as an indicator reaction, said change in colour representing a measurable variable for the amount of bonded analyte molecules. The quantitative determination of the alteration of colour is normally carried out by an optical transmission measurement through the interior volume of the reactor and through the plastic body.

Further embodiments of microreactors consist of a volume through which a flow passes, e.g. a capillary or a flow passage filled with a carrier material, on the inner surface of which (the inner wall or surface of the carrier material) a receptor layer is immobilized. Such a system is described in E. Yacoub-George, H. Wolf, S. Koch, P. Woias, A Miniaturized ISFET-ELISA System with a Pretreated Fused Silica Capillary as Reaction Cartridge, Proc. of the Transducers '95—Eurosensors IX, Stockholm, Sweden, 1995, pp. 898–901. The chemical reaction mechanism used in this case is similar to the above-described course of action and produces as the last step again an indicator reaction in the volume of fluid contained in the reactor. The inner volume of the reactor is then supplied to a subsequent evaluation component, e.g. a photometer or an electrochemical sensor, for carrying out the quantitative determination of the indicator reaction.

Like reactors with an without integrated evaluation components, also a great variety of optical transmission cells is presently used in the field of analytical and synthetic chemistry. Simple embodiments consist of measuring cuvettes which are filled with the liquid to be analyzed and introduced in the ray path of an array comprising a light source and an optical detector. Flow-through cuvettes, however, comprise a flow passage which is introduced in the ray path of the optical array in the direction of flow or transversely to the direction of flow, said optical array consisting of a light source and of an optical detector.

E. Verpoorte, A. Manz, H. Lüdli, H. M. Widmer, B. H. van der Schoot, N. F. de Rooij, A Novel Optical Detector for Use in Miniaturized Total Chemical Analysis Systems, Transducers '91, Book of Abstracts, pp. 796–799, describes a micromechanical flow-through cuvette, which consists of a channel realized by means of anisotropic etching processes and covered on the upper surface thereof by a silicon chip provided with windows. Due to the use of silicon wafers with an <100> crystal orientation, the lateral walls of the channel, which have been produced by anisotropic etching, have the orientation of the etch-resistant <111> crystal plane. As is known to those skilled in the art, this plane extends at an angle of approx. 54° to a horizontal reference plane. In the known micromechanical flow-through cuvette, light is coupled in by being radiated in approximately perpendicularly through an optical entrance window by means of a light waveguide, which is directed onto an inclined end face of the etched channel. Perpendicularly means in this context a direction perpendicular to the direction of flow of the sample fluid. Due to the reflection at one end face of the channel, light is guided into the cell interior and, due to multiple reflections on the lateral walls, it is guided to the second end face, where it is coupled out of the channel through an optical window, i.e. through the cover chip, and fed into a glass fibre arranged at right angles to the direction of flow of the sample fluid. It follows that the light is coupled out at the second end face, the outcoupling glass fibre leading to a detector which may have a conventional structural design.

One disadvantage of commercially available microtitration plates is that they have typical inner volumes of the reactor in the range of some ml and diffusion path lengths in the range of some mm. This has the effect that the development of the chemical processes in the interior of the reactor, i.e. the bonding of the analyte molecules to the receptor layer, the generation of the indicator value, etc., is mainly determined by the comparatively long diffusion paths and the resultant long diffusion times. The time required for an analysis can therefore be in the range of some hours.

Furthermore, microtitration-plate tests are processed by automated anlysis apparatus which must have a comparatively high mechanization degree (e.g. pipetting robots, plate transport mechanisms), whereby the costs and the error rate are increased.

The use of reactors without integrated evaluation components normally requires additional transport steps at the end of the indicator reaction, and these additional transport steps may result in a higher expenditure and, depending on the respective structural design, in signal losses, e.g. due to mixing processes during transport in a flow-through system.

Optical transmission cells operating according to the cuvette principle have a comparatively large fluid volume in the range of some ml and are not suitable for flow-through operation. It follows that automatic processing of sample series can only be carried out with a high mechanical outlay making use of a robot system or of automatic handling machines.

Optical flow-through cuvettes are often produced by conventional techniques, e.g. injection moulding of plastic material, whereby miniaturization is only possible to a certain degree.

The micromechanical flow-through cuvette in silicon technology, which has been mentioned hereinbefore, additionally has, as has been described hereinbefore, an intentionally chosen perpendicular coupling-in direction of the light so that a ray path with multiple reflections on the channel walls is obtained. The large number of multiple reflections is intended to substantially increase the effective optical path length of the cell in comparison with the channel diameter by factors of 10 to 50, whereby an improved detection sensitivity is to be achieved. Since the etched silicon channel walls permit, however, only lossy reflections, a high light power must be coupled into this known transmission measuring cell so that a measurable light power can be coupled out at the outlet.

U.S Pat. No. 4,908,112 discloses a silicon semiconductor wafer for analyzing micronic biological samples. The analytical device comprises a separation channel having an elongate shape, electrodes formed in said channel, and a storage reservoir as well as a reception reservoir. The single separation channel or a plurality of separation channels are formed in a silicon wafer and have bevelled walls which are typically produced when etching by means of a potassium hydroxide solution is carried out. A silicon dioxide layer is formed on the channel. The electrodes are used for activating a movement of the sample fluids through said channel by means of electroosmosis. For analyzing the sample, a laser beam is directed onto a bevelled side wall of the channel; from said bevelled side wall, the laser beam is reflected transversely across the channel transversely to the opposite wall, and from said opposite wall it is reflected out of the channel. By means of the incident laser light, fluorescence is produced in a suitable analytical sample, the fluorescent light emerging from the channel being detected by means of a photodetector. The fluorescent light is used for determining the components of the sample which have been separated by electromigration.

EP 0 488 947 A1 discloses a miniaturized detector cell produced from silicon or quartz. Said detector cell comprises a channel in which a sample fluid is contained as well as an inlet and an outlet window for light for carrying out a transmission measurement. The light is radiated perpendicularly onto an inclined wall of the channel so as to carry out multiple reflections in the channel and in the elongate receptacle, respectively; subsequently, it is directed from the outlet opening to a suitable detector. These multiple reflections increase the length of the interaction path substantially.

DE 41 37 060 A1 discloses a microcuvette for infrared spectroscopy. Said microcuvette comprises a channel and inlet and outlet openings for a sample fluid, which are arranged at right angles to said channel. Light is radiated in directly through silicon discs defining the cuvette.

GB 2 071 355 A discloses a fluid cell which is used for a spectroscopic analysis and which comprises a front plate as an optical window, a rear plate having a reflecting surface, and a sealing means between these two plates. The rear plate is provided with an inlet and an outlet opening for fluids which are to be analyzed in said cell.

Reference 6 (CH 674 082 A5) discloses a cuvette comprising as a main element a prism with a chosen form which consists of a transparent material and the refractive index of which is higher than the refractive index of the solution to be examined. A cavity filled with a fluid to be analyzed is arranged above said prism, where as an empty cavity is located below said prism. In this cuvette, the light propagates substantially in said prism and is influenced by a fluid arranged in side-by-side relation with said prism.

It is the object of the present invention to provide a micromechanical transmission measuring cell which permits a low consumption of sample fluid and reagents and which achieve s a high detection accuracy.

This object is achieved by a micromechanical transmission measuring cell according to claim 1.

The present invention is based on the finding that, for a high detection accuracy, light, which has been coupled into a sample fluid receptacle, must be prevented from being subjected to multiple reflections on the inner wall of the receptacle so as to limit the reflection losses in the sample fluid receptacle to a minimum. Hence, a bundle of quasi-parallel rays, which will be referred to as "light beam" in the following, is used for transmission measurement in the micromechanical transmission cell according to the present invention, the diameter of said "light beam" being smaller than the internal cross-section of the fluid receptacle. This "light beam" is coupled in onto a first reflector in a defined manner in such a way that it passes through the sample fluid receptacle, which can be produced micromechanically in a silicon substrate, largely without any multiple reflections on the receptacle wall. This reflector can be coated e.g. with gold, whereby its reflective properties are optimized. It is not necessary to coat the rest of the inner wall with gold, since only a small amount of the light fed into the receptacle is subjected to multiple reflections on the receptacle wall.

The light used for the measurement may not normally be present in the form of a "light beam", but it may be divergent. In such cases, a collimating lens system can optionally be inserted in the light ray path at a suitable location. This method is generally known from the field of optics. When the divergent light emerging from a light waveguide is used, it will be expedient to apply a gradient lens of suitable length directly onto the end face of the light waveguide.

The micromechanical transmission cell for determining the optical absorption of a sample fluid comprises a receptacle for holding the sample fluid, a light passage opening for introducing the light into the receptacle, and the reflector directing the light relative to the receptacle in such a way that most of said light passes through said receptacle without multiple reflections on a wall of said receptacle.

In comparison with macroscopic reactors, such as the microtitration plate described at the beginning, the micromechanical transmission cell according to the present invention offers the advantage of a small internal volume of the reactor, said advantage being possible due to the micromechanical silicon processing technique. This results in short diffusion paths and diffusion times and in a low consumption of reagents, analyte and sample fluid. The micromechanical transmission cell can be provided with a sample-fluid inlet opening through which a sample fluid is introduced in the receptacle, whereupon said micromechanical transmission cell is operated in the so-called "stopped-flow" mode, i.e. the sample fluid does not flow through said micromechanical transmission cell but it stands still so to speak in said cell. By providing a sample-fluid outlet opening, the micromechanical transmission cell according to the present invention can, however, also be used in a flow-through mode. Hence, it is adapted to be used in a very flexible manner. When an inlet and an outlet opening are provided, "stopped-flow" operation is possible as well. In this case, the reagent is pumped in, whereupon the pump is stopped and the reaction is allowed to take place.

In comparison with reactors without an integrated evaluation component (such as a fused silica capillary), the micromechanical transmission cell permits an in-situ determination of reaction results without additional transports being necessary. Furthermore, reaction developments in the interior volume of the reactor can be determined in situ e.g. by measurements of the reaction kinetics.

As has already been mentioned, the main advantages which the micromechanical transmission cell shows in comparison with the known micromechanical flow-through cuvette including an integrated evaluation component are the minimum amount of reflections in the sample-fluid receptacle resulting from the fact that the ray path is chosen such that it extends parallel or perpendicular to the direction of flow as well as parallel to the receptacle wall, whereby reflection losses of the light transmitted through the receptacle are minimized. Furthermore, the micromechanical transmission cell according to the present invention permits arbitrary combination possibilities of coupling the light in and out and of supplying and discharging the fluid on the upper and on the lower side of the receptacle.

By immobilizing on the inner wall of the receptacle a biochemical component which initiates or influences a chemical reaction in the reactor interior by interaction with an associated reaction partner to be detected, e.g. an enzyme substrate or an antigen, and which produces in this way an optically detectable reaction result that can be correlated with the analyte concentration, the micromechanical transmission cell according to the present invention can also be used as a biochemical reactor, without the transmission being influenced by the reflective properties of the biochemical component on the inner wall of the receptacle. Without immobilizing a biochemical component on the receptacle, the micromechanical transmission cell can be used as a universally usable transmission cell.

In the following, preferred embodiments of the present invention will be explained in more detail making reference to the drawings enclosed, in which.

The micromechanical transmission cell according to the present invention can be used for an integrated optical transmission measurement and be produced and miniaturized fully by the methods used in the field of silicon micromechanics. The micromechanical transmission cell can be used for the following purposes:

on the inner wall of the reactor a biochemical component is immobilized, e.g. an enzyme or a receptor, which, by interaction with an associated reaction partner to be detected, e.g. an enzyme substrate or an antigen, initiates or influences a chemical reaction in the interior of the reactor and produces an optically detectable reaction result in this way, which can be correlated with the analyte concentration.

In addition, the micromechanical transmission cell according to the present invention can be used as a universally applicable transmission cell without immobilizing a biochemical component. By means of the small internal volume that can be realized, temporally and locally resolved measurements can be carried out much better than by means of macroscopic cells. For example, the development of a chemical reaction in the interior of the cell through which the reaction medium flows can be supervised directly on the basis of an optically detectable reaction result. The reaction kinetics can be observed directly in this way, and, if necessary, it can be controlled during the measurement, i.e. on-line, by choosing suitable reaction parameters, such as the flow rate and the mixing ratio of the reagents before the cell.

Figure 1:
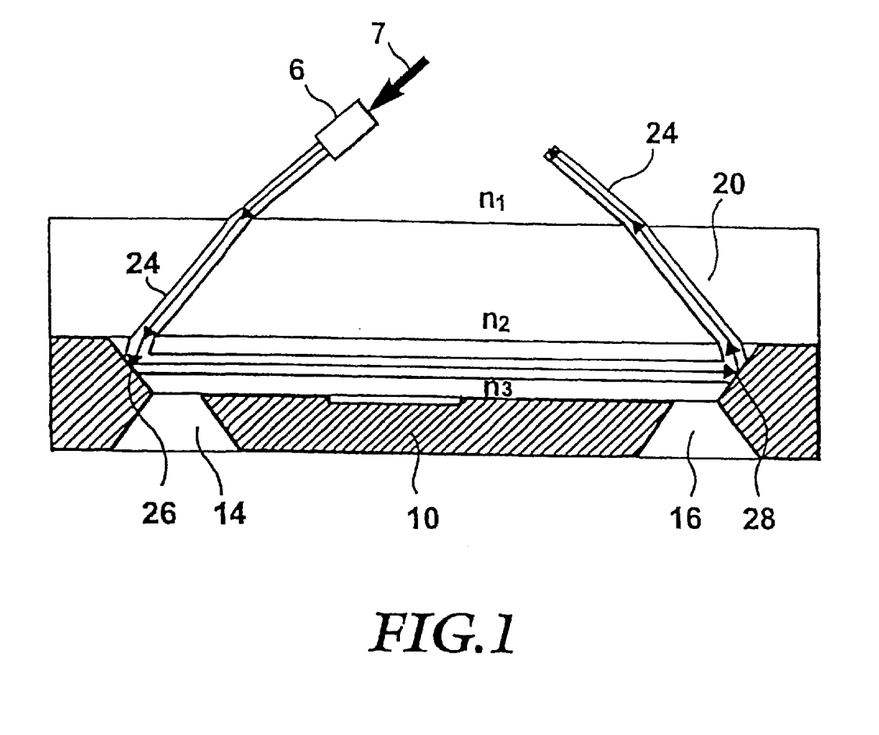
FIG. 1 shows a basic structure of the transmission cell with inclined walls at the end faces of a receptacle and with light coupled in from a light waveguide.
Figure 2:
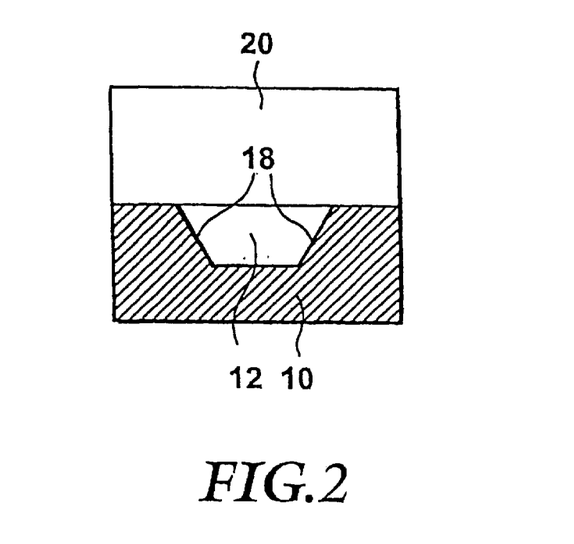
FIG. 2 shows a basic structure of the reactor with inclined walls at the lateral surfaces of the receptacle.

FIG. 1 and FIG. 2 show the fundamental fluidic concept of the micromechanical transmission cell according to the present invention. FIG. 1 represents a longitudinal section through the cell 12, whereas FIG. 2 shows a cross-sectional view thereof. In a substrate 10 consisting preferably of silicon a receptacle 12 is formed. A sample fluid can be introduced into the receptacle 12 via an inlet opening 14; said sample fluid can flow out of the receptacle 12 through an outlet opening 16. As can be seen in FIG. 1 and FIG. 2, the inlet opening 14 and the outlet opening 16 as well as the receptacle 12 have inclined walls 18, 26 which are produced by means of known anisotropic etching processes for silicon, e.g. by means of etching with a potassium hydroxide solution. At this point, it should be pointed out that the inlet and outlet openings 14, 16 do not need inclined walls. To those skilled in the art, it is obvious that the anisotropic etching with potassium hydroxide solution will provide comparatively smooth inclined walls 18, 26 which are also suitable for reflecting light without any scattering which would be worth mentioning.

When the micromechanical transmission cell is provided with the inlet opening 14 as well as with the outlet opening 16, the receptacle 12 serves as a sample fluid channel. On the side located opposite the substrate 10, the receptacle 12 is closed by a cover 20. From the further description, it will be apparent that the cross-sectional shape and the longitudinal-sectional shape of the receptacle 12 are of no importance as long as light is directed into the receptacle 12 in such a way that multiple reflections of the light on the walls are avoided as far as possible.

FIG. 1 shows, by way of example, the transformation of a bundle of divergent rays emerging from a light waveguide 7 into a bundle of quasi-parallel rays 24 ("light beam") with the aid of a gradient lens 6.

Figure 3:
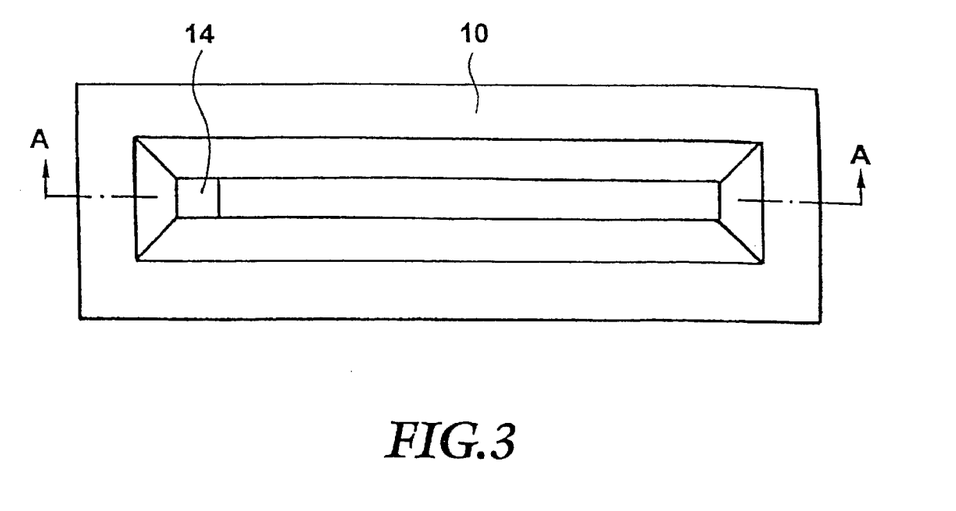
FIG. 3 shows a top view of the micromechanical transmission cell of FIG. 1 in the case of which the cover has been removed.

As can be seen in FIG. 3, the receptacle 12 of the optical transmission cell according to the present invention has preferably an elongate shape. In particular FIG. 3 shows a top view of the micromechanical transmission cell according to the present invention in the case of which the cover 20 has been omitted. In this variant, an inlet opening 14 for introducing a sample fluid into the receptacle 12 is formed through the silicon substrate 10. As can be seen from FIG. 4, said silicon substrate 10 has, however, not formed therein the outlet opening 16 as well, as can be seen in FIG. 1, but said outlet opening 16 is formed in the cover 20.

The cover 20, which closes the receptacle on the upper side of the substrate, should consist of a suitable material which, depending on the way in which the light is coupled in, which will be described hereinbelow, must be optically transparent at least in certain areas thereof. Glass could, for example, be used as a suitable material for the cover 20. With the exception of the optically transparent windows required for coupling the light in and out, the whole inner wall of the receptacle, preferably, however, only the inclined walls 18 used as mirror surfaces and reflecting means, respectively, can be coated so as to achieve an optimum optical reflectance behaviour. A suitable coating material for silicon is e.g. gold.

Figure 4:
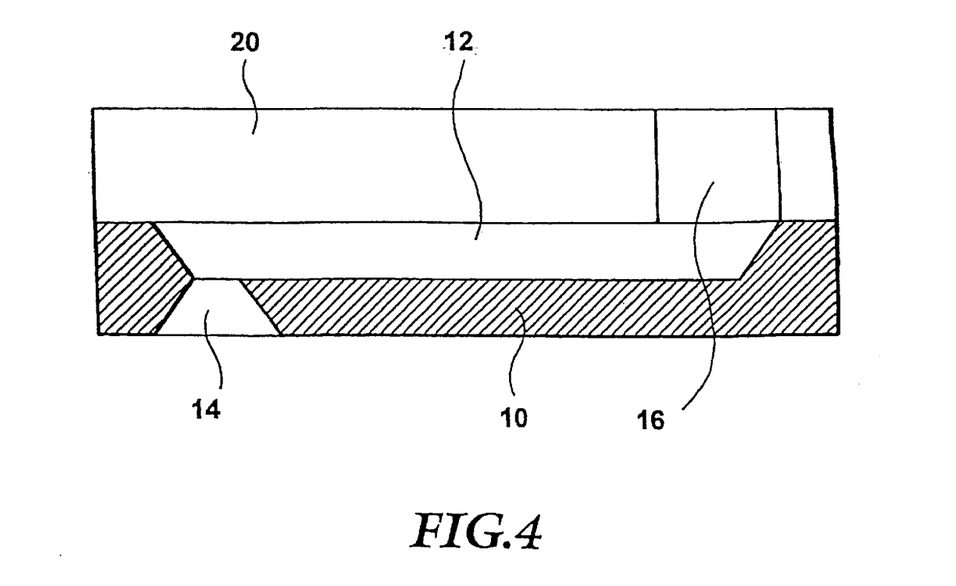
FIG. 4 shows a cross-sectional view of the micromechanical transmission cell of FIG. 3, in which an inlet and an outlet opening are shown directly below and directly above the receptacle.

As will be apparent from a comparison between FIG. 4 and FIG. 1, the supply means and the discharge means of the receptacle 12 can be combined in an arbitrary manner. The supply means and the discharge means can be realized either on the back of the substrate 10 or in the cover 20.

Figure 5:
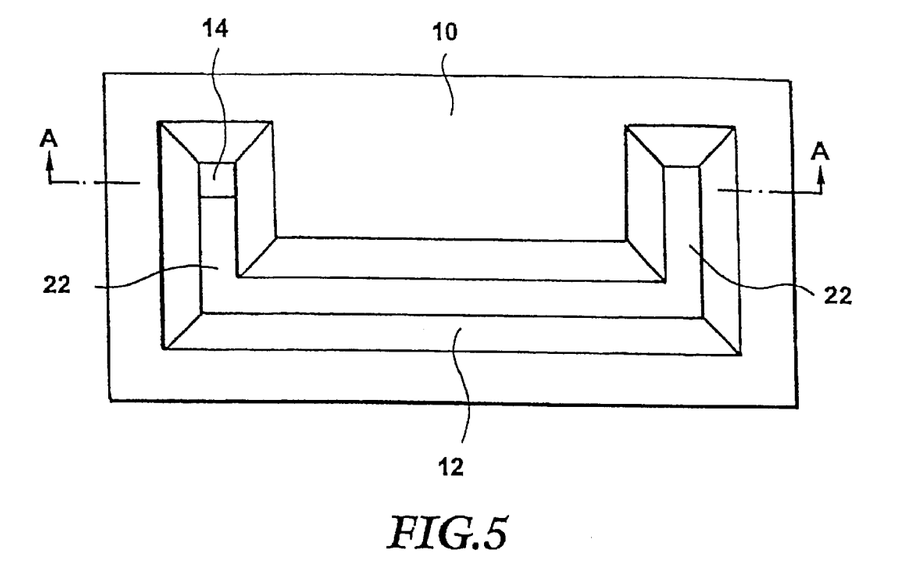
FIG. 5 shows a top view of a transmission cell which has been modified with respect to FIG. 4 and which is provided with a lateral inlet.
Figure 6:
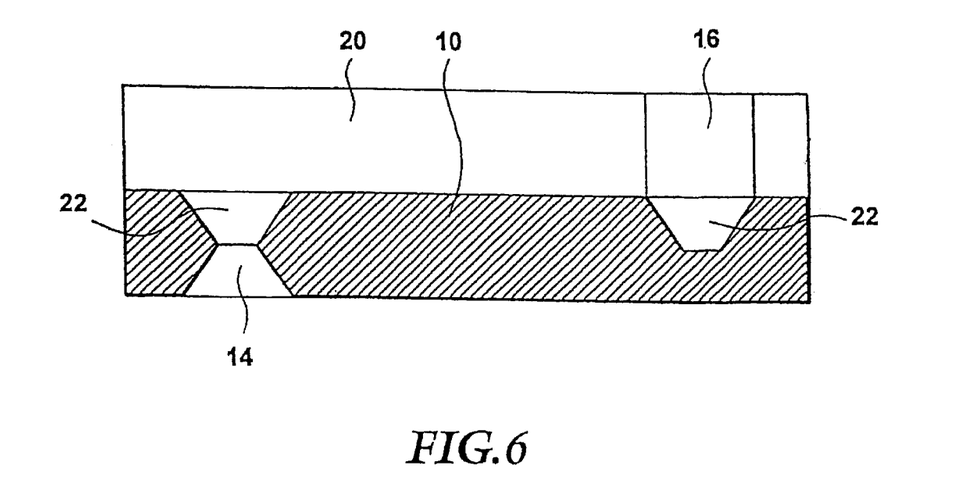
FIG. 6 shows a cross-sectional view along the line A—A of FIG. 5.

As can be seen in FIG. 5 and FIG. 6, FIG. 6 being a cross-section along line A—A of FIG. 5, the inlet opening 14 and the outlet opening 16 (FIG. 6) can also be arranged at the side of the receptacle 12, each of said inlet and outlet openings being then connected by means of a short supply channel 22 to the receptacle 12.

Figure 7:
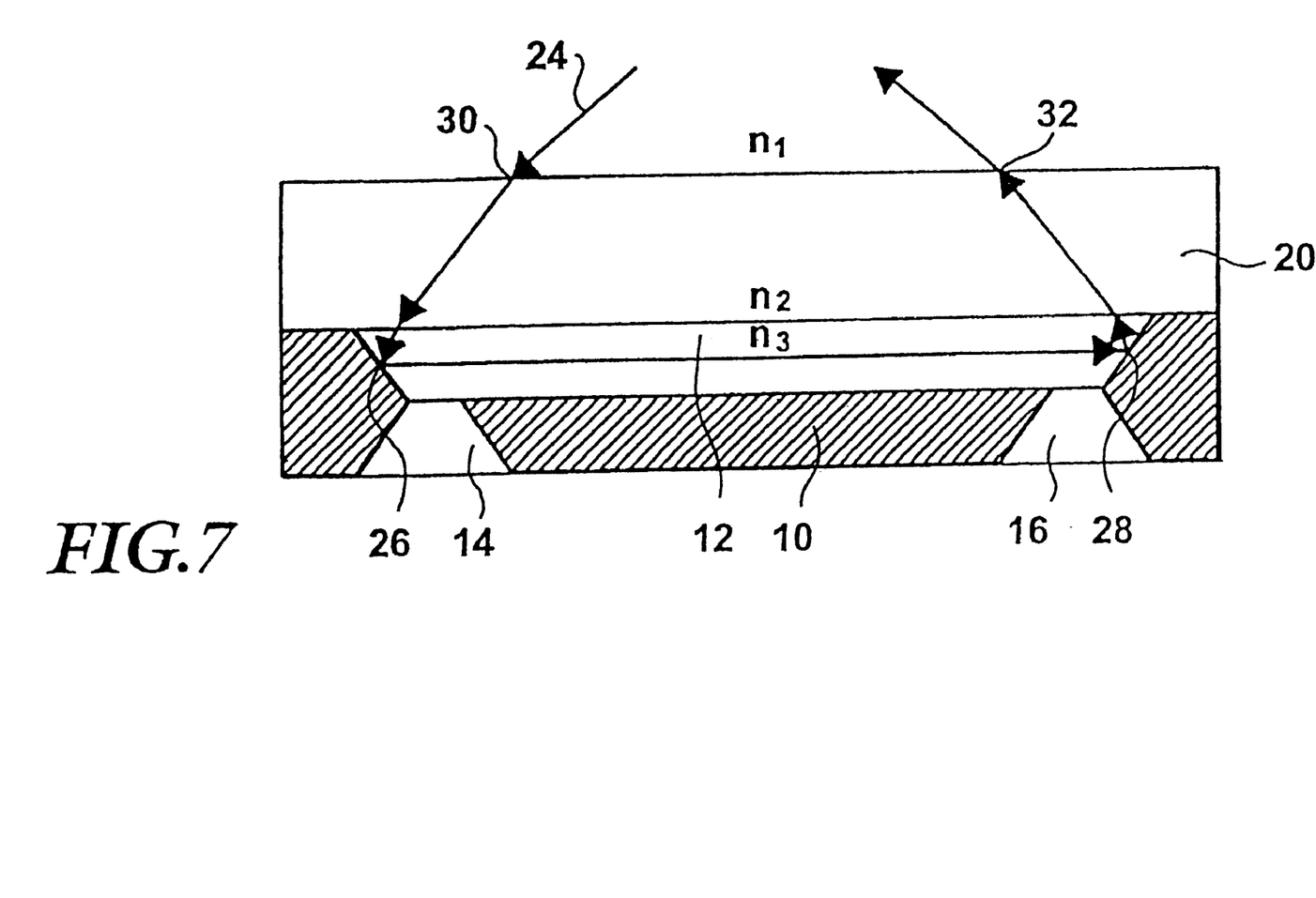
FIG. 7 shows a micromechanical transmission cell according to a first embodiment of the present invention.

FIG. 7 shows a representation of the function of the micromechanical transmission cell according to a first embodiment of the present invention. The "light beam" 24, which is schematically shown by a sequence of rays, is radiated onto a reflector 26 at a defined angle. In the embodiment of the micromechanical transmission cell shown in FIG. 7, the reflector 26 is realized as an inclined wall of the receptacle 12; said wall can be coated with a highly reflective layer, e.g. with gold, so as to achieve an optimum reflectance behaviour.

The "light beam" 24 (also referred to as the "light" 24 in the following) is radiated from a first medium having a refractive index $n_1$, which can e.g. be air, into the optically transparent cover 20 having a refractive index $n_2$ and from said cover 20 into the sample fluid having the refractive index $n_3$ so that it will be directed from the reflector 26 essentially parallel to one of the receptacle walls, which is realized by the substrate 10, and the other receptacle wall, which is realized by the lower surface of the cover 20, to a further reflector 28, which can again be realized by an inclined wall of the receptacle 12 and which can optionally be coated with gold. From said further reflector 28, the light will again be directed from the sample fluid having the refractive index $n_3$ into the optically transparent cover having the refractive index $n_2$ and from said cover into the outer medium having the refractive index $n_1$, which can be air, as can be seen in FIG. 7.

It follows that the optically transparent cover 20 in FIG. 7 acts as a light passage opening 30 for coupling the light into the receptacle 12 and, simultaneously, as a further light passage opening 32 so that the light can re-emerge from the receptacle 12. To those skilled in the art it will be apparent that it is not absolutely necessary that the whole cover consists of a transparent material, but that said cover can, for example, also be produced from the substrate material 10, e.g. silicon; in this case, said cover must, however, include a transparent window as light passage opening 30 and also a correspondingly implemented transparent window for the additional light passage opening 32. If no "light beam", i.e. no fully collimated light is available, the light will, however, be directed approximately parallel to the boundary walls of the receptacle 12 due to the coupling in of the light 24 onto the reflector 26, in such a way that most of the light 24 will pass through the receptacle 12 without multiple reflections on a wall of said receptacle. In this case, it may be appropriate to provide the complete lateral walls of the receptacle with a highly reflective layer, e.g. gold. Hence, an essential aspect of the present invention is that the light 24 propagates substantially parallel to the surface of the substrate 10 defining the lower wall of the receptacle 12 with respect to FIG. 7.

The inclination of the reflector 26 and of the additional reflector 28 with regard to the longitudinal direction of the receptacle 12 can be determined by the anisotropic etching with a potassium hydroxide solution, whereby an inclination angle of approx. 55° is obtained. Inclined walls with other angles of inclination or reflectors which are formed separately in the sample fluid receptacle can, however, also be used for the transmission cell according to the present invention as long as most of the light radiated into the sample fluid receptacle passes through said receptacle without multiple reflections on the receptacle wall. By means of the incoupling angle of the light beam 24 into the transparent cover 20, any desired incident angle of the light 24 on the reflector 26 can be achieved in such a way that the beam is guided essentially parallel to the substrate 10, whereby only a small amount of multiple reflections on a wall of the receptacle 12 will occur so that optical losses in the receptacle 12 will be limited to a minimum. It follows that due to the incoupling angle of the light 24 into the optically transparent cover any refractive index $n_3$ of the sample fluid can be compensated for, whereby the optical transmission cell according to the present invention is very flexible in use so as to obtain always the best possible parallel guidance of the light.

The determination of the transmitted light intensity, i.e. of the light, emerging through the further light passage opening 32 from the cover 20, is carried out with the aid of a detection method known to those skilled in the art.

Figure 8:
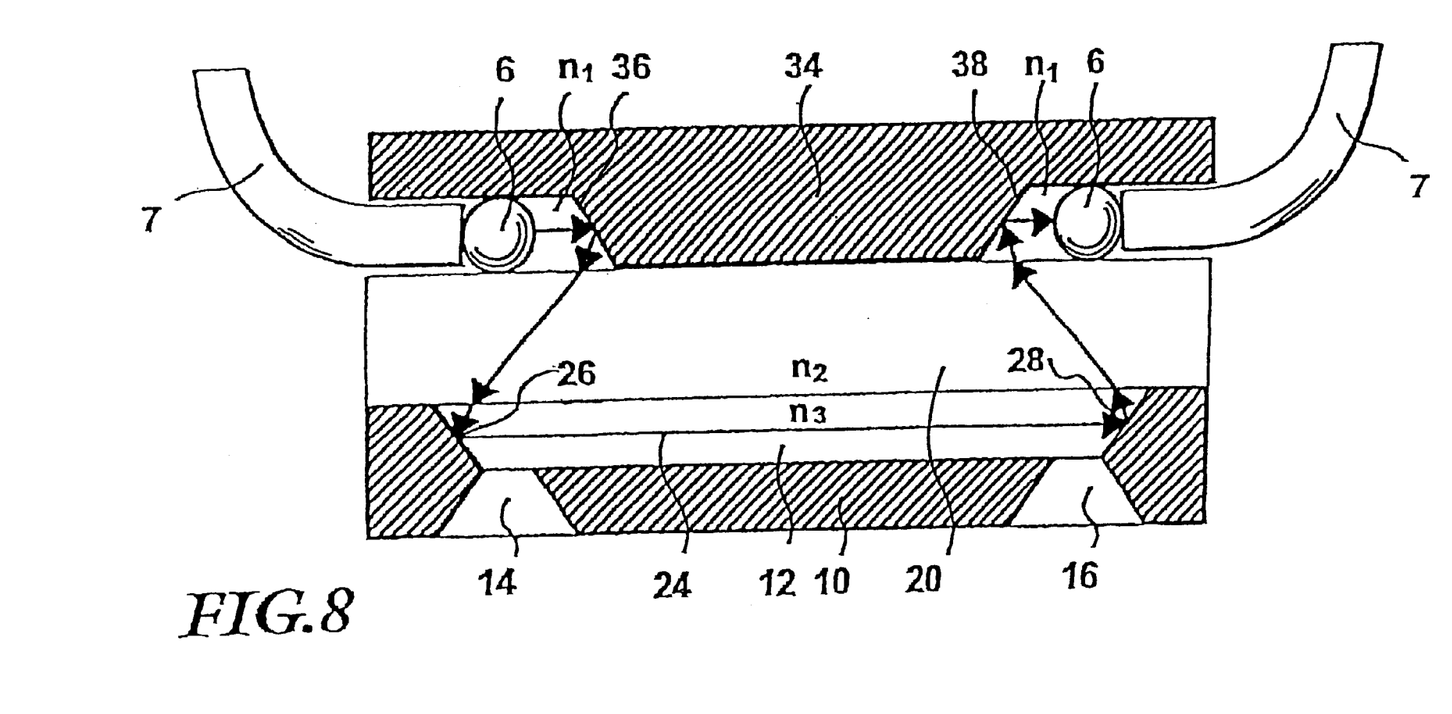
FIG. 8 shows a micromechanical transmission cell according to a second embodiment of the present invention provided with an integrated incoupling and outcoupling optics for light waveguides.

FIG. 8 shows a second embodiment of the optical transmission cell according to the present invention. In comparison with the first embodiment shown in FIG. 7, the second embodiment is additionally provided with an in/outcoupling means 34 for light waveguides, said in/outcoupling means comprising an incoupling mirror 36, an outcoupling mirror 38 and two spherical lenses 6 as well as the two light waveguides 7. Preferably, the in/outcoupling means also consists of a silicon chip, the incoupling mirror 36 as well as the outcoupling mirror 38 being realized as inclined lateral surfaces and the light waveguides 7 and the lenses 6 being positioned in a self-adjusting manner in recesses etched in a V-shape, as can be seen in FIG. 8.

Optionally, the incoupling mirror 36 as well as the outcoupling mirror 38 can be coated e.g. with gold so as to optimize the reflectance behaviour of the mirrors.

The optical refractive index $n_1$ between the in- and outcoupling locations and the respective first reflection point can be adapted to the refractive index $n_3$ of the medium in the channel so as to achieve a precisely axis-parallel coupling in of the light. This adaptation can be achieved e.g. by optically transparent casting compounds or liquids in the space designated by reference symbol $n_1$ in FIG. 8. The refractive index $n_2$ of the cover 20 produces under these circumstances only a parallel displacement of the light beams, which can be taken into consideration upon designing the optical transmission cell according to the second embodiment of the present invention.

In comparison with the first embodiment shown in FIG. 7, the embodiment shown in FIG. 8 additionally shows the advantage that the error rate with respect to an incorrect incoupling angle in the optically transparent cover 20 is markedly reduced in the case of the second embodiment, since the second embodiment shown in FIG. 8 always permits coupling in in an orientation parallel to the substrate 10 and to the in/outcoupling means 34, the refractive index $n_3$ being so to speak structurally taken into account by the medium with the refractive index $n_1$, as has already been mentioned.

Figure 9:
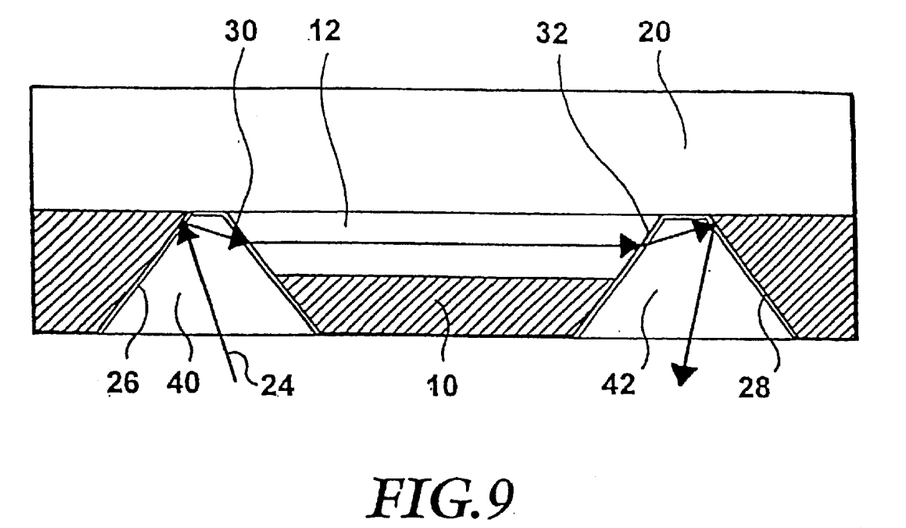
FIG. 9 shows a micromechanical transmission cell according to a third embodiment of the present invention.

FIG. 9 shows a third embodiment of the micromechanical transmission cell according to the present invention. In this embodiment, the light 24 is coupled in and out on the back of the substrate 10, and, consequently, it is no longer necessary that the cover 20 is optically transparent. In order to permit the light 24 to be coupled in onto the reflector 26, a light shaft 40 is produced in the substrate 10. Coupling out of the light 24 is carried out through a further light shaft 42, which is also produced in the substrate 10, as can be seen in FIG. 9. The light shaft 40 and the additional light shaft 42 are implemented as etched recesses, which adjoin the end faces of the receptacle 12 or opposed locations of the receptacle walls and which are each provided with an optically transparent membrane facing towards the receptacle. Hence, the optically transparent membrane 30 serves as a light passage opening, whereas the optically transparent membrane 32 serves as an additional light passage opening for coupling the light 24 out from the receptacle 12. Coupling in and coupling out of the light is carried out by reflection on the reflector 26 and on the further reflector 28, respectively, which are implemented as inclined walls in the light shaft 40 and in the additional light shaft 42. The incident angle of the light 24, the incident plane and the locations of incidence are again chosen such that a ray path parallel to the surface of the substrate 10 and either parallel (end face incidence) to or perpendicular (side incidence) to the direction of flow of the sample fluid will be formed in the receptacle 12, said sample fluid being introduced in and discharged from the receptacle 12 e.g. by the lateral configuration shown in FIG. 5 or FIG. 6.

Figure 10:
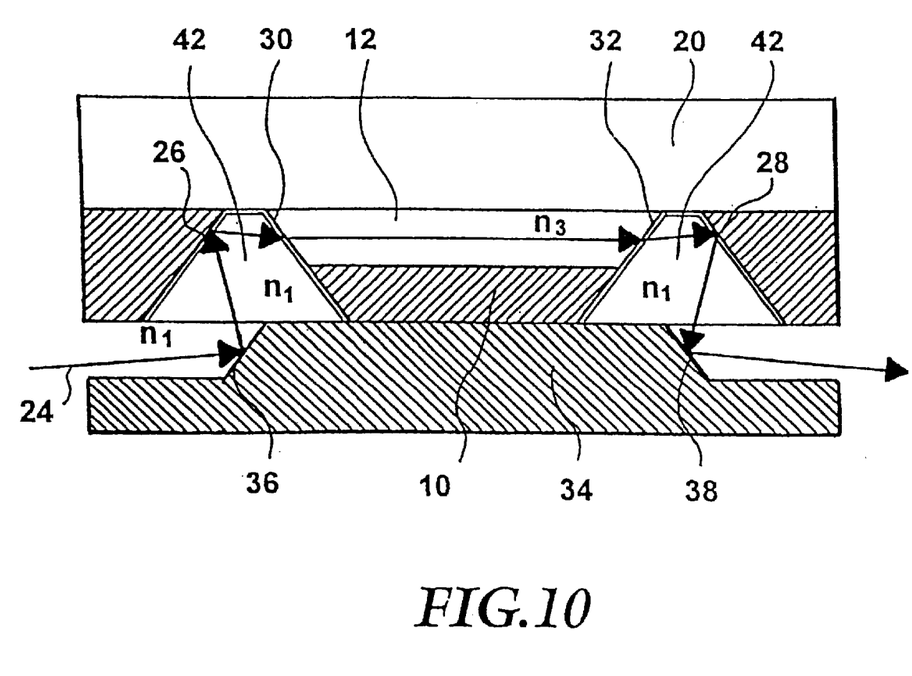
FIG. 10 shows a micromechanical transmission cell according to a fourth embodiment of the present invention.

FIG. 10 shows a fourth embodiment of the optical transmission cell according to the present invention, which is similar to the second embodiment shown in FIG. 8, the light 24 being now, however, directed from the back of the substrate 10 via the incoupling mirror of the in/outcoupling means 34 through the light passage opening 30 and the additional light passage opening 32 onto the further reflector 28 and from said further reflector 28 onto the outcoupling mirror 38 so that it will leave the transmission cell. For obtaining an optimum parallel ray path in the receptacle 12, a material having a specific refractive index $n_1$ can be used for filling the light shafts 40 and 42, as has already been described with respect to FIG. 8.

Deviating from the embodiments described hereinbefore, e.g. the additional reflector 28 could be replaced by a light passage opening provided e.g. by means of a micromechanical bore in the substrate 10 so that the light 24 can be guided out of the receptacle 12 without any second reflection in said receptacle 12.

Furthermore, the additional reflector 28 might be implemented as a vertical mirror instead of being implemented as an inclined wall for directing the light 24 into the cover 20, whereby the light 24, after having been coupled in onto the reflector 26 and after its parallel propagation through the receptacle, will completely be reflected back along the same path and emerge from the receptacle 12 along a path corresponding to the incoupling path due to a reflection on the reflector. Persons skilled in the art know how an optical beam passing back and forth can be separated, e.g. by optical filter means.

What is claimed is:

1. A micromechanical transmission measuring cell for determining an optical absorption of a sample fluid, comprising:
    a receptacle formed in a substrate and used for holding the sample fluid, said receptacle having an elongate shape with a longitudinal axis;
    a light passage opening for introducing the light into the receptacle; and
    a reflector defined by a wall which has been produced by anisotropic etching of the substrate,
    wherein the reflector is inclined relative to the longitudinal direction of the receptacle in such a way that the light, which impinges on the surface of the substrate at an angle relative to said surface, is reflected along the longitudinal axis to an opposite wall, most of said light passing through said receptacle without multiple reflections on a wall of said receptacle, and that the optical absorption of the sample fluid is detectable on the basis of the light passing through said receptacle without multiple reflections,
    wherein a beam transformation of fed-in light into a bundle of substantially parallel rays is effected by a lens, whereas a further lens reverses this process.

2. The micromechanical transmission measuring cell according to claim 1,
    wherein the substrate consists of silicon.

3. The micromechanical transmission measuring cell according to claim 1,
    wherein the receptacle is closed by a cover.

4. The micromechanical transmission measuring cell according to claim 1,
    comprising in addition an inlet opening in the substrate for introducing the sample fluid into the receptacle.

5. The micromechanical transmission cell according to claim 4, comprising in addition an outlet opening for the sample fluid, said outlet opening being formed in said substrate or in a receptacle cover so as permit sample fluid to flow through said receptacle.

6. The micromechanical transmission measuring cell according to claim 1, further comprising:
    a further reflector arranged remote from said reflector in the path of the light through the receptacle and directing the light, which has been directed relative to said receptacle, out of said receptacle; and
    a further light passage opening through which the light that has been directed by means of the further reflector emerges from the receptacle.

7. The micromechanical transmission measuring cell according to claim 6,
    wherein the light passage opening and the additional light passage opening are formed by means of the cover consisting of a material which is transparent to the light.

8. The micromechanical transmission measuring cell according to claim 1,
    wherein a biochemical component is immobilized on an inner wall of the receptacle, which, by interaction with a reaction partner to be detected in the sample fluid, causes a chemical reaction which provides an optically detectable reaction result.

9. The micromechanical transmission measuring cell according to claim 1, and further including an additional reflector, and wherein the reflector and the additional reflector, respectively, are provided with a highly reflective coating.

10. The micromechanical transmission measuring cell according to claim 1,
    wherein the inner walls of the receptacle are provided fully or partly with a highly reflective coating.

11. A micromechanical transmission measuring cell for determining an optical absorption of a sample fluid, comprising:
    a receptacle formed in a substrate and used for holding the sample fluid, said receptacle having an elongate shape with a longitudinal axis;
    a light passage opening for introducing the light into the receptacle; and
    a reflector defined by a wall which has been produced by anisotropic etching of the substrate, wherein the reflector is inclined relative to the longitudinal direction of the receptacle in such a way that the light, which impinges on the surface of the substrate at an angle relative to said surface, is reflected along the longitudinal axis to an opposite wall, most of said light passing through said receptacle without multiple reflections on a wall of said receptacle, and that the optical absorption of the sample fluid is detectable on the basis of the light passing through said receptacle without multiple reflections, a further reflector arranged remote from said reflector in the path of the light through the receptacle and directing the light, which has been directed relative to said receptacle, out of said receptacle;

a further light passage opening through which the light that has been directed by means of the further reflector emerges from the receptacle; and wherein the light passage opening and the additional light passage opening are formed by means of a cover consisting of a material which is transparent to the light, wherein an in/outcoupler is arranged on the side of the cover located opposite the receptacle, said in/outcoupler comprising an incoupling mirror and an outcoupling mirror which are inclined relative to the light passage openings in such a way that light can be coupled into and out of the transmission measuring cell in the direction in which it propagates in the receptacle for the sample fluid.

12. A micromechanical transmission measuring cell for determining an optical absorption of a sample fluid, comprising:

a receptacle formed in a substrate and used for holding the sample fluid, said receptacle having an elongate shape with a longitudinal axis;

a light passage opening for introducing the light into the receptacle; and a reflector defined by a wall which has been produced by anisotropic etching of the substrate, wherein the reflector is inclined relative to the longitudinal direction of the receptacle in such a way that the light, which impinges on the surface of the substrate at an angle relative to said surface, is reflected along the longitudinal axis to an opposite wall, most of said light passing through said receptacle without multiple reflections on a wall of said receptacle, and that the optical absorption of the sample fluid is detectable on the basis of the light passing through said receptacle without multiple reflections, and wherein the reflector is arranged outside of the receptacle in a light shaft formed in the substrate.

13. The micromechanical transmission measuring cell according to claim 12, further comprising:

a further light passage opening through which the light passing through the receptacle emerges from said receptacle;

a further reflector which is formed in an additional light shaft and by means of which the light passing through said further light passage opening is directed away from the substrate.

14. The micromechanical transmission measuring cell according to claim 12, and further including a receptacle cover, wherein said cover is not transparent to said light.

15. The micromechanical transmission measuring cell according to claim 13, wherein an in/outcoupler, which comprises an incoupling mirror and an outcoupling mirror, is arranged in the vicinity of the light shafts, said incoupling mirror and said outcoupling mirror being inclined relative to the reflector and the additional reflector in such a way that the light can be coupled into and out of the micromechanical transmission measuring cell in the direction in which it passes through the receptacle for the sample fluid.

* * * * *